US00PP23516P3

(12) United States Plant Patent
Fazio et al.

(10) Patent No.: US PP23,516 P3
(45) Date of Patent: Apr. 9, 2013

(54) APPLE TREE ROOTSTOCK NAMED 'G.214'

(50) Latin Name: *Malus domestica×Malus robusta hybrid*
Varietal Denomination: G.214

(75) Inventors: Gennaro Fazio, Geneva, NY (US); James Cummins, Geneva, NY (US); Herbert Sanders Aldwinckle, Geneva, NY (US); Terence Lee Robinson, Geneva, NY (US)

(73) Assignees: Cornell University, Ithaca, NY (US); The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/927,537

(22) Filed: Nov. 17, 2010

(65) Prior Publication Data

US 2012/0124707 P1 May 17, 2012

(51) Int. Cl.
*A01H 5/00* (2006.01)

(52) U.S. Cl. ..... Plt./174

(58) Field of Classification Search ..... Plt./174
See application file for complete search history.

(56) References Cited

U.S. PATENT DOCUMENTS

| | | | |
|---|---|---|---|
| PP7,714 | P | 11/1991 | Masseron et al. |
| PP7,715 | P | 11/1991 | Masseron et al. |
| PP11,070 | P | 9/1999 | Cummins et al. |
| PP12,443 | P2 | 3/2002 | Cummins et al. |
| PP17,063 | P3 | 8/2006 | Cummins et al. |
| PP17,139 | P3 | 10/2006 | Cummins et al. |
| PP18,618 | P2 | 3/2008 | Alston |
| PP21,223 | P3 | 8/2010 | Budagovsky |
| 2002/0002717 | P1 | 1/2002 | Yoshida et al. |
| 2006/0130195 | P1 | 6/2006 | Cummins et al. |
| 2006/0174386 | P1 | 8/2006 | Cummins et al. |
| 2006/0174387 | P1 | 8/2006 | Cummins et al. |
| 2010/0132081 | P1 | 5/2010 | Budagovsky et al. |

OTHER PUBLICATIONS

"Cornell Gardening Resources, Apple Tree Rootstocks," Ecogardening Factsheet #21, Cornell University, Department of Horticulture, Summer 1999, http://www.gardening.cornell.edu/factsheets/ecogardening/appleroot.html.

Cummins Nursery Catalog 2004, Rootstocks, Updated Feb. 2011, Ithaca, NY, http://www.cumminsnursery.com/rootstocks.htm.

Domoto, P., "Characteristics of Apple Rootstocks," Iowa State University, Department of Horticulture, Nov. 2004, http://www.nc140.org/2004/domotorootstock.pdf.

Norelli, J.L. et al., "Resistance of Geneva and Other Apple Rootstocks to Erwinia Amylovora," Plant Disease, 2003 pp. 26-32, vol. 87, No. 26.

United States Department of Agriculture, Agricultural Research Service, "The National Apple Rootstock Breeding Program," Feb. 2011, Geneva, NY, http://ars.usda.gov/Main/docts.htm?docid=15654.

*Primary Examiner* — Susan McCormick Ewoldt
(74) *Attorney, Agent, or Firm* — MacMillan, Sobanski & Todd, LLC

(57) ABSTRACT

A new and distinct variety of apple tree rootstock *Malus domestica×Malus robusta* hybrid 'G.214' is described herein. The new variety is a dwarfing rootstock that is resistant to fire blight (*Erwinia amylovora*) and crown rot (*Phytophthora cactorum*). The 'G.214' rootstock is useful in that it can be propagated clonally and used as a rootstock or root system for apple trees as well as for interstems of apple trees.

5 Drawing Sheets

STATEMENT REGARDING FEDERAL FUNDING

Research related to this invention was funded under USDA ARS CRADA, Sponsor's Contract #:58-3K95-9-1358-M; the U.S. government may have rights herein.

Genus and species: *Malus domestica×Malus robusta* hybrid.

Variety denomination: 'G.214'.

BACKGROUND OF THE INVENTION

I. Field & Utility Summary

The present invention relates to a new and distinct variety of apple tree. The apple tree is particularly useful in that it can be propagated clonally and used as a rootstock or root system for apple trees as well as for interstems of apple trees.

II. Cultivation Summary

'G.214' originated from a planned cross in 1975 in Geneva, N.Y.

III. Comparisons

The seed parent *Malus domestica* 'Ottawa 3' is a dwarfing rootstock, i.e., trees grown on this rootstock are 30 to 35 percent the size of a standard tree grafted on an apple seedling rootstock. 'Ottawa 3' is known to induce good precocity in the scion (i.e., the ability to induce early reproductive development in the scion) and has high yield efficiency. 'Ottawa 3' plants produce no spines, are fairly well anchored, are very cold hardy rootstocks and have resistance to crown and root rot caused by *Phytophthora cactorum*. However, 'Ottawa 3' is susceptible to the woolly apple aphid (*Eriosoma lanigerum*) and to fire blight (*Erwinia amylovora*).

The pollen parent *Malus robusta* 'Robusta 5' is a non-dwarfing rootstock, i.e. trees on this rootstock are the same size as a standard tree grafted on an apple seedling rootstock. 'Robusta 5' does not induce precocity in the scion and is not highly yield efficient. Juvenile plants of 'Robusta 5' produce many spines. 'Robusta 5' breaks buds very early in the spring and is winter hardy. It is resistant to powdery mildew (*Podosphaera leucotricha*) and fire blight, and is immune to the woolly apple aphid. Further, 'Robusta 5' has shown tolerance to the specific replant disease complex.

The 'G.214' apple rootstock of the present invention has a combination of qualities that distinguishes it from its parental plants (i.e., 'Ottawa 3' and 'Robusta 5'). For example, unlike the well-anchored 'Ottawa 3' parent, 'G.214' is a poorly anchored rootstock. 'G.214' has dwarfing properties derived from 'Ottawa 3', and belongs to the same dwarfing vigor class as its dwarfing parent (i.e., 'Ottawa 3'). Specifically, 'G.214' has dwarfing characteristics that are similar to the industry standard of *Malus domestica* 'Malling 9'. 'G.214' shares further similarities with 'Ottawa 3' in that they both induce precocity to the scion, are highly yield efficient, winter hardy, and resistant to crown and root rot caused by *Phytophthora cactorum*.

With regard to its 'Robusta 5' parent, 'G.214' is distinguishable in that it is a dwarfing rootstock and is highly yield efficient, whereas 'Robusta 5' is not. However, like 'Robusta 5', 'G.214' is resistant to fire blight, powdery mildew, and the woolly apple aphid (*Eriosoma lanigerum*). In addition, 'G.214' has been shown to have some tolerance to the replant disease complex.

As discussed above, 'G.214' is most similar to 'Malling 9' in terms of dwarfing class. However, 'G.214' is resistant to fire blight whereas 'Malling 9' and other rootstocks in its market class are not.

With regard to apple tree rootstock 'G.935', a variety from the same parents as 'G.214', 'G.214' is resistant to wooly apple aphid (*Eriosoma lanigerum*)and 'G.935' is susceptible.

IV. Breeding History

In the spring of 1975, pollen from a *Malus robusta* 'Robusta 5' apple tree was applied to emasculated flowers of a *Malus domestica* 'Ottawa 3' apple in Geneva, N.Y. In the fall of 1975, approximately 500 seeds resulting from this pollination were extracted from mature fruit derived from this cross. In the winter of 1975-76, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1976, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #214 was one of the survivors of this battery of inoculations from the same cross. All the surviving plants were in Geneva, N.Y. in the fall of 1976 and allowed to grow side shoots for propagation/evaluation. In 1978, 'G.214' was evaluated for rooting ability, lack of spine production, and low root brittleness in a layering bed (stool bed). In 1982, 4 finished trees with 'G.214' rootstock were planted in Geneva, N.Y. with *Malus domestica* cv. 'Northern Spy' grafted onto this rootstock as the scion cultivar. This rootstock performed well (top 20% of many rootstocks tested) in these first test trials and in 1988 more material was propagated by stool bed and nursery to be entered into new trials in Geneva, N.Y. with *Malus domestica* cv. Empire as the scion cultivar. The 'G.214' rootstock performed well with all the scion cultivars that were tested. In August of 2002, several rootstock liners of 'G.214' were budded with 15 different scion cultivars to test graft union compatibility the test results showed that 'G.214' was compatible with all the cultivars tested. In summer 2002, 40 rootstock liners were inoculated with four different strains of *Erwinia amylovora*, the fire blight bacterium (ten liners per strain in Geneva, N.Y. As a result, the apple rootstock 'G.214' was classified as immune to two of the strains tested and moderately resistant to the other two strains of *Erwinia amylovora*.

V. Asexual Reproduction

Asexual reproduction of the 'G.214' apple rootstock has been achieved using the traditional method of clonally propagating apple rootstocks. In particular, the original seedling of the 'G.214' apple rootstock was planted in Geneva, N.Y. and allowed to develop into a "mother plant." The 'G.214' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.214' apple rootstock variety has been asexually reproduced by root cuttings, by budding and grafting onto seedling and clonal rootstocks, and by tissue culture.

VI. Stability

Observations of trees from these propagations indicate that all trees have proven true to type and identical in all appearances to the original tree.

SUMMARY OF THE INVENTION

The present invention relates to a new and distinct variety of apple tree rootstock named 'G.214.' The 'G.214' apple tree rootstock is a dwarfing rootstock that is resistant to fire blight (*Erwinia amylovora*) and crown rot (*Phytophthora cactorum*). The 'G.214' rootstock is useful in that it can be propagated clonally and used as a rootstock or root system for apple trees as well as for interstems of apple trees. The apple tree rootstock 'G.214' is as dwarfing as 'Ottawa 3' and more dwarfing than the non-dwarfing parent 'Robusta 5'. Unlike 'Ottawa 3', 'G.214' is resistant to fire blight. Although 'G.214' is in the same dwarfing market class as 'Malling 9', it is distinguishable from 'Malling 9' because 'G.214' is resistant to fire blight whereas 'Malling 9' is susceptible.

DETAILED BOTANICAL DESCRIPTION

Figure 1:
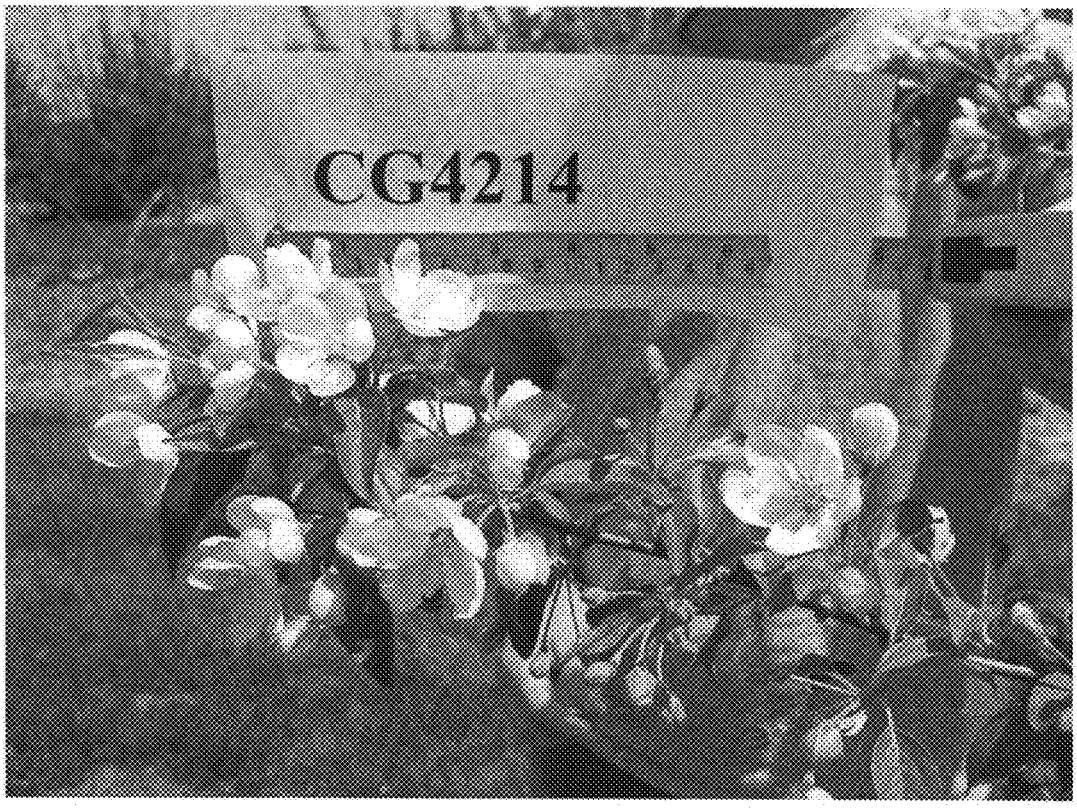
FIG. 1 shows flowers of G.214 at open and balloon stage.
Figure 2:
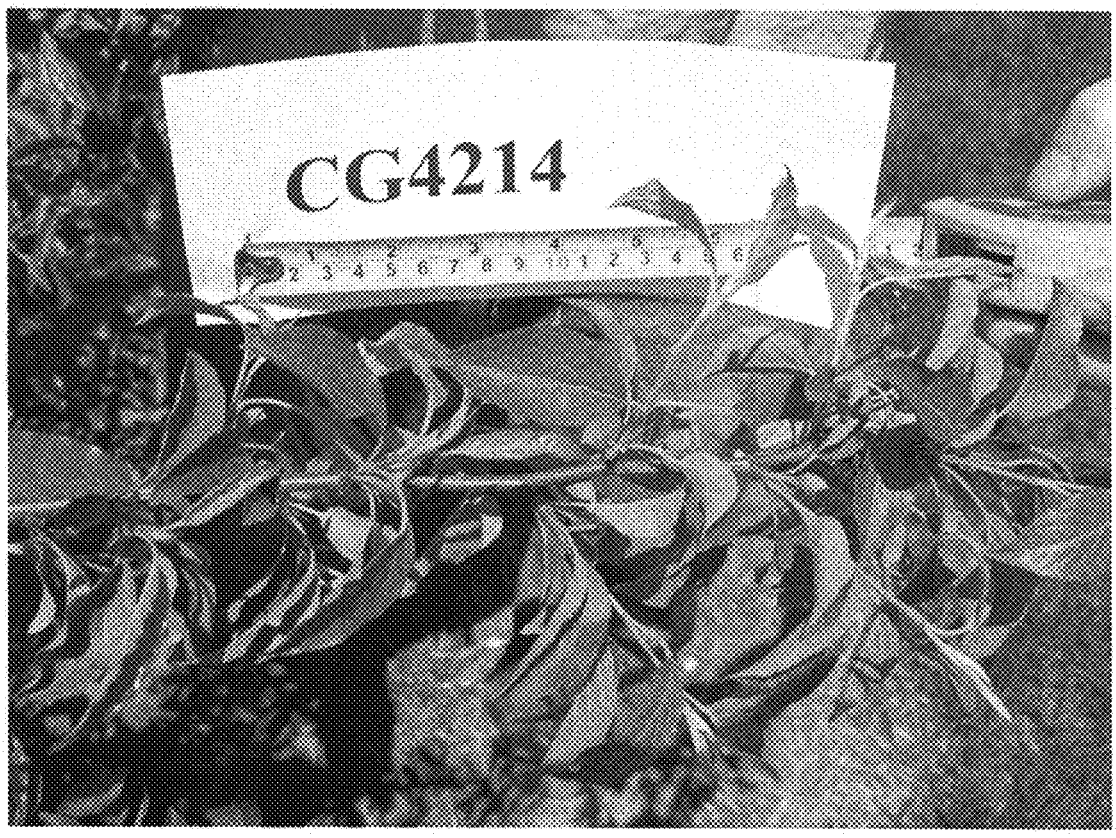
FIG. 2 shows bark and leaves of G.214.
Figure 3:
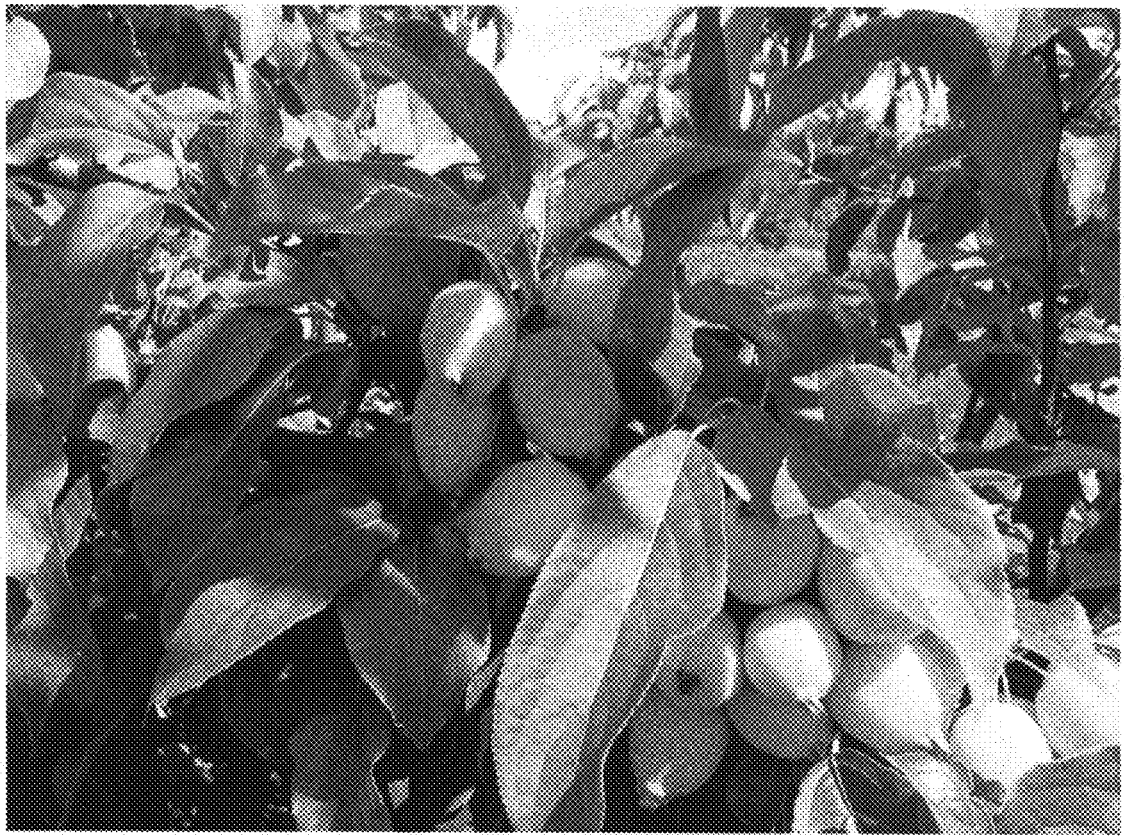
FIG. 3 shows fruit and leaves of G.214.
Figure 4:
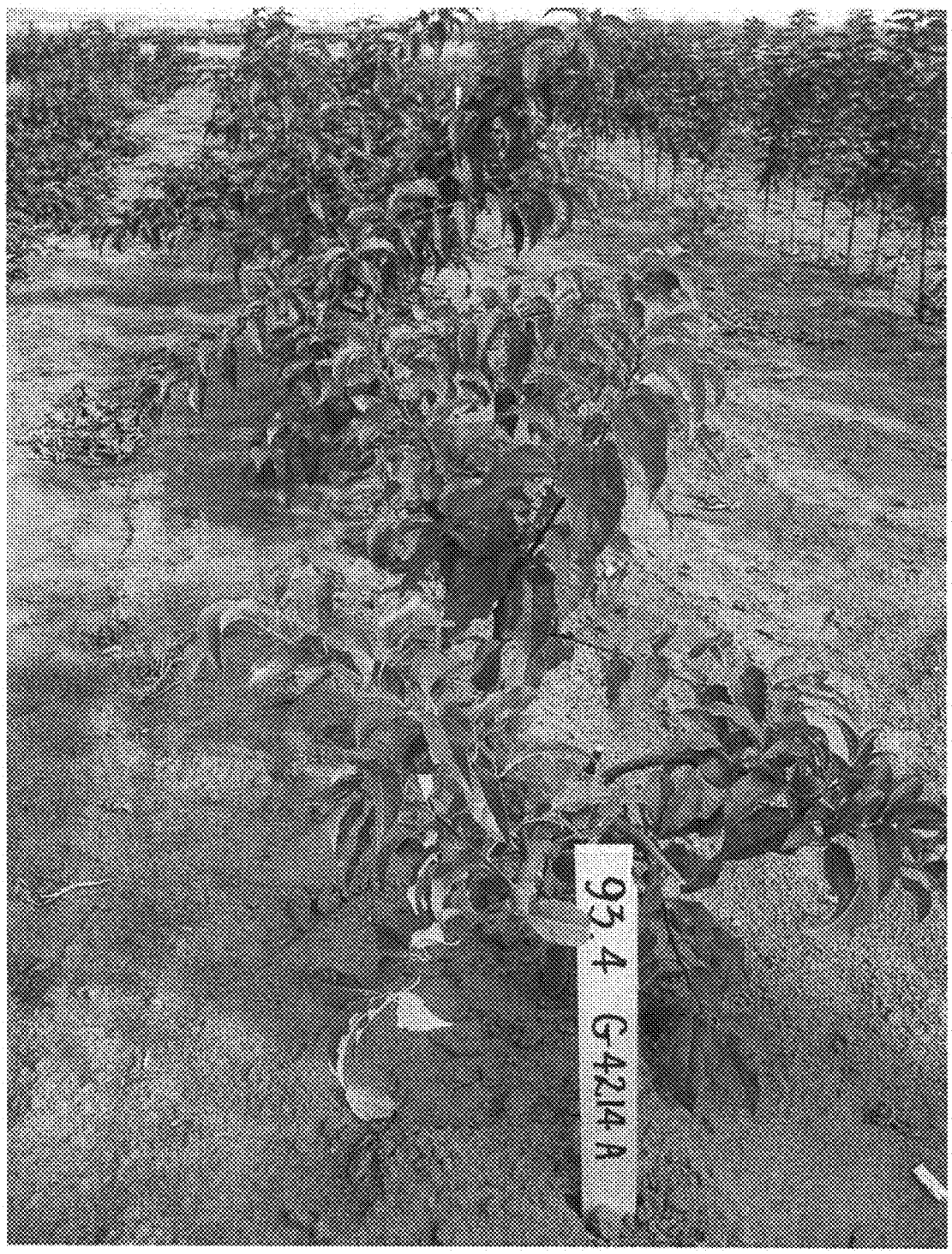
FIG. 4 shows liners of G.214 in a finished tree nursery.
Figure 5:
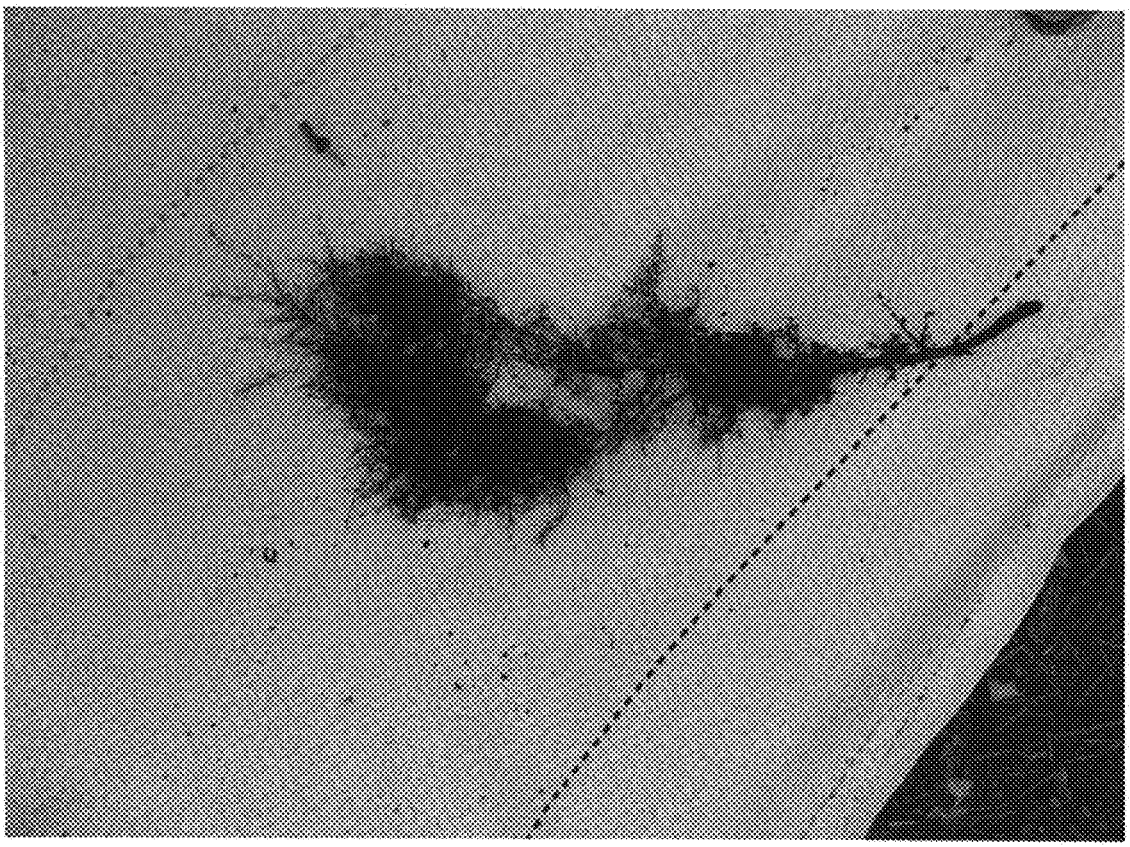
FIG. 5 shows fine root system of G.214.

The following description of 'G.214' contains references to color names taken from The Royal Horticultural Society Colour Chart (R.H.S.), 2001 edition. Botanical descriptions follow the Manual of Cultivated Plants (Bailey, 1949).

Tree:

*Habit*.—A self-rooted tree of 'G.214' is a small shrub typically standing about 1.5-2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season. The apical bud in these plants is pubescent Greyed-Green (RHS 191D).

*Root system*.—The 'G.214' exhibits very dense root system due to the presence of high branching of fine roots (less than 3 mm in diameter) when compared to other dwarfing rootstocks such as Malling 9 or Malling 26 which lack this trait.

*Productivity*.—In an intermediate trial performed in Geneva, N.Y., the 'G.214' rootstock received the cultivar 'Empire' (*Malus domestica*) as the scion and was compared to the *Malus domestica* check rootstocks M.9 EMLA, M.26 and M.7. 'G.214' was shown to have statistically higher ($p \leqq 0.05$) yield efficiency (kg yield/$cm^2$ trunk cross sectional area) than all the check rootstocks.

*Precocity*.—Scion cultivars budded on 'G.214' exhibit the same precocity as those budded on M.9.

*Fertility* (*Fecundity*).—The 'G.214' plant produces flowers and fruits regularly.

Dormant shoots (buds and bark):

*Dormant mature shoots*.—Color: Greyed-Red (RHS 178A) where exposed to full sunlight grading to Greyed-Orange (RHS 173B) with diminished light exposure. Texture: Very light pubescence which gradually disappears in older tissues. Size: 30-60 cm long; may have some spines.

*Axillary buds*.—Size: 2-3 mm long and 3 mm wide with little pubescence. Shape: Obtuse, sessile, somewhat appressed and flattened. Texture: Some pubescence.

*Bark on three-year-old shoots*.—Color: Greyed-Green (RHS 197A). Lenticels: Color: Greyed-Orange (RHS 163B). Size: 0.3-0.4 mm in diameter. Quantity: 1-2 lenticels per $cm^2$.

Leaves:

*Mature leaves*.—Leaf arrangement: Alternate. Shape: Simple, recurved, oblong-ovate. Size: Length: 85 mm. Width: 50 mm at the widest point. Laminae: Somewhat wavy. Apex: Acuminate. Base: Nearly symmetrical rounded. Margin: Acutely serrated, with about 5 serrations per cm. Upper surface: Color: Green (RHS 126B). Texture: Glabrous and translucent. Lower surface: Color: Green (RHS 146C). Texture: Somewhat pubescent. Venation: Netted. Leaf poise: 15°-25° from the shoot, depending on shoot orientation. Stipules: Length: 8 mm. Width: 2 mm. Petioles: Diameter: 2 mm. Color: Gradation of Green (RHS 140A) to Greyed-Red (RHS 179A) depending on low or high exposure to light.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot (a short shoot associated with a flower cluster). Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Size: Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs*.—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit*.—Size: Height: 30-35 mm. Diameter: 30-35 mm. Shape: Obloid. Color: Partial Yellow-Orange skin (RHS 22A) with Red (RHS 46C) blush overtones depending on the exposure to the sun. Sepals: Persisting on a very protruding calyx. Flesh: Taste: Astringent (not meant for consumption). Color: Yellow-Orange (RHS 17C). Seed: Color: Greyed-Red (RHS 179A), translucent. Shape: Tear drop shape. Size: Length: 50-60 mm. Diameter: 25-35 mm at the widest point. Number: Generally five seed per fruit.

Disease resistance: As described above, the 'G.214' rootstock of the present invention exhibits resistance to fire blight. The percent lesion measured after inoculation of potted liners in the greenhouse using four different strains of *Erwinia amylovora* was negligible for two of the strains and moderate for the other two, indicating a specific resistance to the bacterium. The 'G.214' rootstock, having survived the inoculation with crown and root rot, is also considered resistant to crown and root rots caused by *Phytophthora cactorum*.

We claim:

1. A new and distinct variety of apple tree rootstock named 'G.214' as herein described and illustrated.

* * * * *